(12) United States Patent
Bajramovic et al.

(10) Patent No.: US 11,766,171 B2
(45) Date of Patent: Sep. 26, 2023

(54) METHOD FOR THE CONTINUOUS CONTROL OF THE FIXATION OF A PATIENT'S EYE DURING THE DETECTION OF BIOMETRIC MEASUREMENT DATA OF THE PATIENT'S EYE

(71) Applicant: Carl Zeiss Meditec AG, Jena (DE)

(72) Inventors: Ferid Bajramovic, Mamming (DE); Wei-Jun Chen, Jena (DE); Tobias Bühren, Ulm (DE)

(73) Assignee: Carl Zeiss Meditec AG, Jena (DE)

( * ) Notice: Subject to any disclaimer, the term of this patent is extended or adjusted under 35 U.S.C. 154(b) by 694 days.

(21) Appl. No.: 16/962,508

(22) PCT Filed: Jan. 17, 2019

(86) PCT No.: PCT/EP2019/051090
§ 371 (c)(1),
(2) Date: Jul. 15, 2020

(87) PCT Pub. No.: WO2019/141750
PCT Pub. Date: Jul. 25, 2019

(65) Prior Publication Data
US 2021/0076934 A1    Mar. 18, 2021

(30) Foreign Application Priority Data
Jan. 19, 2018    (DE) .................... 10 2018 200 829.9

(51) Int. Cl.
*A61B 3/10*    (2006.01)
*A61B 3/00*    (2006.01)
*A61B 3/113*    (2006.01)

(52) U.S. Cl.
CPC ............ *A61B 3/102* (2013.01); *A61B 3/0008* (2013.01); *A61B 3/1005* (2013.01); *A61B 3/113* (2013.01)

(58) Field of Classification Search
CPC ..... A61B 3/102; A61B 3/0008; A61B 3/1005; A61B 3/113
(Continued)

(56) References Cited

U.S. PATENT DOCUMENTS 7,284,858 B2 * 10/2007 Bergner ................. A61B 3/112
                                                      351/208
7,470,025 B2    12/2008 Iwanaga
(Continued)

FOREIGN PATENT DOCUMENTS

DE    10 2012 019 473 A1    6/2014
WO    WO 2015/116981 A1    8/2015

OTHER PUBLICATIONS

International Search Report for PCT/EP2019/051090, dated May 21, 2019, 2 pages.
(Continued)

*Primary Examiner* — Mohammed A Hasan
(74) *Attorney, Agent, or Firm* — DeWitt LLP

(57) ABSTRACT

A method for capturing biometric measurement data of a patient's eye, in which the fixation is monitored during the entire biometric measurement. Information in respect of the fixation is extracted, depending on the different recording modes, from already available or additionally captured recordings and/or data. Central retinal OCT scans with absolute fixation information and frontal images with relative fixation information with or without at least partial diffuse lighting are used. On the basis of this extracted fixation information, the subsequent evaluation only uses the captured biometric measurement data captured just before, at the same time as or just after frontal images with the correct fixation. The method can also be applied to different measurement tasks, in which use is made of different mea- (Continued)

surement modes and in which the alignment of the measurement object is important for the measurement results.

21 Claims, 3 Drawing Sheets

(58) Field of Classification Search
USPC .......................................................... 351/206
See application file for complete search history.

(56) References Cited

U.S. PATENT DOCUMENTS

| | | | |
|---|---|---|---|
| 7,887,185 B2 * | 2/2011 | Barth | G01B 11/14 |
| | | | 351/205 |
| 9,492,079 B2 | 11/2016 | Walsh et al. | |
| 2010/0238405 A1 * | 9/2010 | Newman | A61B 5/0066 |
| | | | 351/200 |
| 2012/0069302 A1 | 3/2012 | Juhasz et al. | |
| 2012/0133889 A1 | 5/2012 | Bergt et al. | |

OTHER PUBLICATIONS

English translation of International Search Report for PCT/EP2019/051090, dated May 21, 2019, 2 pages.
German Search Report for 10 2017 223 216.1 dated Nov. 9, 2018, 12 pages.

* cited by examiner

METHOD FOR THE CONTINUOUS CONTROL OF THE FIXATION OF A PATIENT'S EYE DURING THE DETECTION OF BIOMETRIC MEASUREMENT DATA OF THE PATIENT'S EYE

RELATED APPLICATIONS

This application is a National Phase entry of PCT Application No. PCT/EP2019/051900 filed Jan. 17, 2019, which application claims the benefit of priority to DE Application No. 10 2018 200 829.9, Jan. 19, 2018, the entire disclosures of which are incorporated herein by reference.

FIELD OF THE INVENTION

The present invention relates to a method for capturing biometric measurement data of a patient's eye, in which the fixation is monitored during the entire biometric measurement where possible.

BACKGROUND

Fixation is important for recording data correctly or for correct measurements in ophthalmic diagnostic and therapy devices, in particular in optical biometrics, keratometry and topography. However, perfect fixation throughout is unrealistic even for cooperative, healthy patients since eye movements cannot be avoided despite different fixation marks.

The extent to which these fixation errors resulting from the eye movements have an effect on the measurement results depends on the respective measurement method as these have different tolerances for eye movement.

In many patients, eye movement will cause fixation errors to exceed the tolerance of the respective measurement method. Fixation can be consistently too poor, particularly in patients with impaired vision. In the case of measurements for optical biometrics, for example, measurement errors as a result of lacking fixation may lead to a suboptimally ascertained refractive power of the IOL to be implanted and may ultimately lead to a deterioration in the refraction of the patient following cataract surgery.

The known prior art has firstly disclosed solutions for keeping the patient's attention as high as possible in order to avoid, or at least minimize, involuntary eye movements.

By way of example DE 10 2009 007 732 A1 describes an arrangement for presenting a fixation mark for ophthalmic examination and/or treatment devices. Here, the fixation mark offered to the patient is modified such that the arising beam structure is energetically and/or temporally and/or spatially and/or spectrally alterable. What the movable fixation mark achieves is that the patient aligns their eye thereon and is able to follow the fixation mark without problems, i.e., without great demands on their concentration.

It was found that such solutions are only suitable for short-term examinations or measurements of the eye. However, should these be prolonged, involuntary eye movements may even arise in the case of cooperative, healthy patients.

Secondly, the known prior art has disclosed solutions in which there is a test of absolute fixation and/or a controlled refixation of the patient.

To this end, DE 10 2012 019 473 A1 describes, for example, a method for reliably determining the axis length of an eye by application of optical coherence tomography (OCT), with, in this case, the alignment of the measuring device with respect to the eye being monitored for all one- or two-dimensional scans in order to be able to ensure a reliable determination of the axis length of the eye.

In particular, B-scans are realized following the alignment of the visual axis of the eye on the principal measurement axis of the measuring device, retinal tissue structures being detected in said B-scans in order to determine the axis lengths which are then used to detect the fovea in order to monitor the alignment. The axis lengths ascertained from the B-scans are then confirmed or corrected and output on the basis of the ascertained position of the fovea or the lateral distance of the latter from the optical axis of the measuring device.

A disadvantage of what is proposed here is that the fixation information cannot be transferred to other times.

SUMMARY OF THE INVENTION

The present invention is based on the object of developing a solution in which the fixation can be monitored as a part of recording measurement data, or in parallel therewith, in order to check the quality of recorded measurement data and, ideally, in order also to compensate fixation errors. In the process, the fixation should be checked and/or compensated as continuously as possible, to be precise without this substantially extending the recording of the measurement data.

According to the invention, this object is achieved by the method for monitoring the fixation of a patient's eye throughout the capture of its biometric measurement data, by way of the following method steps:
  a) recording a central retinal OCT scan with absolute fixation information,
  b) recording a frontal image with relative fixation information at the same time as, or immediately before or after, the central retinal OCT scan with at least partly diffuse lighting,
  c) recording further frontal images with relative fixation information as continuously as possible over time,
  d) checking the fixation state on the basis of the central retinal OCT scan,
  e) should a correct fixation be present, the latter is also assumed for the frontal image recorded in method step b),
  f) calculating a difference vector for each frontal image recorded in method step c), said difference vector describing the deviations from the frontal image recorded in method step b),
  g) comparing the calculated difference vectors of the frontal images recorded in method step c) with a defined threshold, wherein
  h) a correct fixation for the recorded frontal images is assumed if the thresholds are undershot and no correct fixation is assumed if the thresholds are overshot and
  i) use is only made of the biometric measurement data captured just before, at the same time as or just after the frontal images with the correct fixation.

Although the method according to the invention is provided, for example, for capturing biometric measurement data of a patient's eye, it can also be applied to different measurement tasks, in which use is made of different measurement modes and in which the alignment of the measurement object is important for the measurement results.

BRIEF DESCRIPTION OF THE DRAWINGS

The invention is described in more detail below on the basis of exemplary embodiments. In this respect.

DETAILED DESCRIPTION

In the case of the proposed method for monitoring the fixation of a patient's eye throughout the capture of its biometric measurement data, information relating to the fixation is extracted, depending on the different recording modes, from already available or additionally captured recordings and/or data.

According to the invention, the method can be subdivided into the following method steps:
  a) recording a central retinal OCT scan with absolute fixation information,
  b) recording a frontal image with relative fixation information at the same time as, or immediately before or after, the central retinal OCT scan with at least partly diffuse lighting,
  c) recording further frontal images with relative fixation information as continuously as possible over time,
  d) checking the fixation state on the basis of the central retinal OCT scan,
  e) should a correct fixation be present, the latter is also assumed for the frontal image recorded in method step b),
  f) calculating a difference vector for each frontal image recorded in method step c), said difference vector describing the deviations from the frontal image recorded in method step b),
  g) comparing the calculated difference vectors of the frontal images recorded in method step c) with a defined threshold, wherein
  h) a correct fixation for the recorded frontal images is assumed if the thresholds are undershot and no correct fixation is assumed if the thresholds are overshot and
  i) use is only made of the biometric measurement data captured just before, at the same time as or just after the frontal images with the correct fixation.

In method step a), a central retinal OCT scan is realized along the optical axis of the measuring device. This OCT scan with a lateral scanning in the region of the retina contains absolute fixation information and consequently facilitates monitoring of the fixation of the eye to be measured.

What is important here is that the central retinal OCT scan containing absolute fixation information is recorded at a favorable time, at which there is a high probability of a correct fixation.

Depending on the overall duration of the actual biometric measurement, it is expedient to realize the central retinal OCT scan multiple times, i.e., as often as possible.

Figure 1:
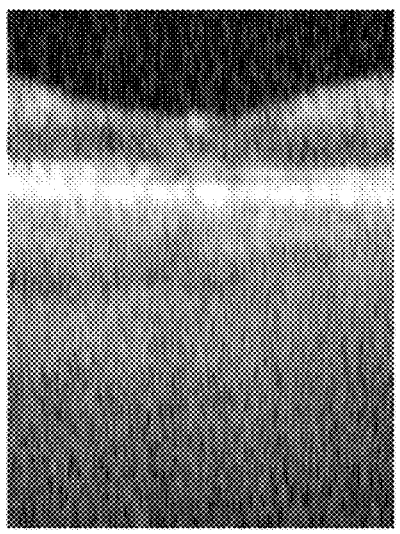
FIG. 1: depicts two examples of central retinal OCT scans with different fixation.
Figure 1:
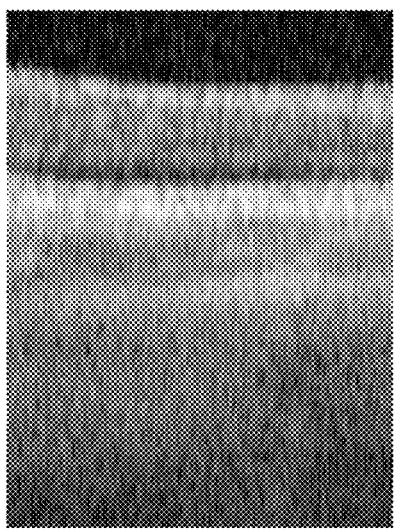

In this respect, FIG. 1 shows an example of such a scan with correct fixation and an example of such a scan with incorrect fixation.

Since the left image representation shows a retinal OCT scan containing the foveal pit in its center, this scan was recorded with the correct fixation. In contrast thereto, the right image representation shows a retinal OCT scan not containing the foveal pit. A correct fixation was not present when this scan was recorded. However, the foveal pit might not be visible in the right image representation because there are morphological changes in this eye.

In the event of the central retinal OCT scan not containing the foveal pit in the result of method step d), and hence in the event of no correct fixation being present, the operator receives an appropriate notification. Then, the method is restarted with method step a), either by the operator or automatically.

To record such retinal OCT scans, which are also referred to as fixation check scans, use can be made of, e.g., the IOLMaster 700 by Carl Zeiss Meditec AG.

Even though the patient is offered a fixation stimulus, for example in the form of a fixation light point, while the measurement data are recorded, there are involuntary eye movements even in the case of cooperative healthy patients. Therefore, it is important to monitor the fixation, not only at a fixed time but throughout the entire process of recording measurement data.

In general, eye movements consist of rotation and translation in three-dimensional space. Depending on the available data recording modes, it is possible to ascertain different ones of these six degrees of freedom.

However, technical reasons may preclude the possibility of also always recording central retinal OCT scans in parallel with the recording of measurement data. Temporally close alternating recording can be restricted from a technical point of view by the switching time between different data recording modes. Additionally, the recording duration of these scans may unfavorably increase the overall time taken for recording the measurement data.

According to the invention, a frontal image with relative fixation information is recorded in method step b) at the same time as, or immediately before or after, the central retinal OCT scan with at least partly diffuse lighting.

By way of example, the lateral translation can be ascertained from this frontal image as a displacement of the structures in the image. Depending on the imaging optical unit employed, the axial translation may also be identifiable as a scaling of the structures in the image or, in the case of telecentric imaging, purely as defocusing.

Here, it is particularly advantageous if an additional reflection is generated on the cornea for the frontal image to be recorded in method step b). This additionally generated reflection is for example generated near the vertex and in a further example at the vertex by projection of a collimated light beam along the optical axis of the device.

This additionally generated reflection on the cornea moreover allows ascertainment of rotation components for the so-called pitching and yawing.

For the evaluation of the relative fixation information, it is advantageous to fit a circular ring to the limbus or to the pupil. As a result, it is possible to detect the change in the position of the light spot relative to other structures in the image, for example the center of this circular ring.

Figure 2:
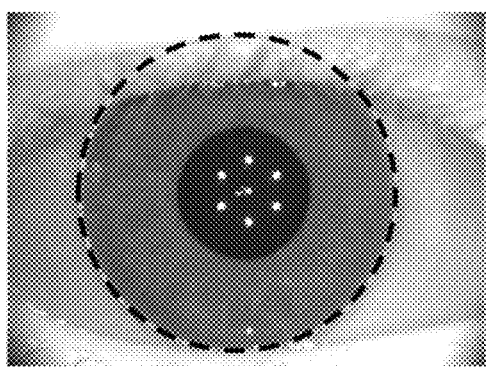
FIG. 2: depicts two frontal images with light spot patterns reflected by the cornea in the case of at least partly diffuse lighting at different fixations.
Figure 2:
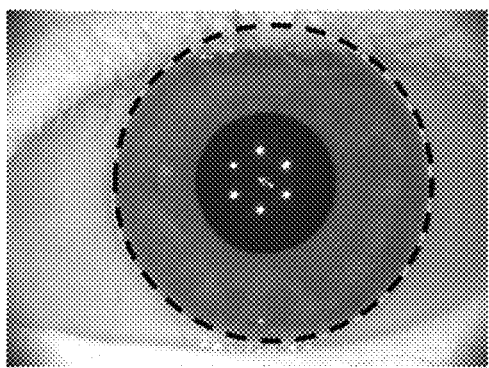

To this end, FIG. 2 shows two frontal images in the case of at least partly diffuse lighting, with a circular ring fitted to the limbus and with different fixations.

In particular, the distance here between the center of the circle of the limbus and the additional reflection on the cornea depends on the fixation direction, as can be identified from the difference between the left and right image representation.

Therefore, this modality allows ascertainment of temporal changes in the fixation direction. This results from the fact that structures in the eye at different depths are displaced relative to one another in the camera image when there is a change of the fixation direction.

During the further course of the method, further frontal images with relative fixation information are recorded as continuously as possible over time as per method step c). According to the invention, these frontal images are recorded under different lighting situations, depending on the recording modes.

To this end, a fast switchover between these recording modes is important. By way of example, this can be achieved by virtue of camera-based recording modes being switched over purely by changing the lighting, with the change in lighting for example being implemented so as to be synchronized with the camera trigger.

Depending on which recording modes can run parallel in time and which can be switched over quickly or only slowly, different temporal arrangements of the different data recordings are expedient.

By way of example, use is made here of frontal images which show a light spot pattern that has been reflected by the cornea. Here, too, lateral translation movements can be ascertained in the case of telecentric observation. In general, it is not possible to ascertain rotation from this type of frontal images, especially since the cornea of the eye is almost spherical.

Figure 3:
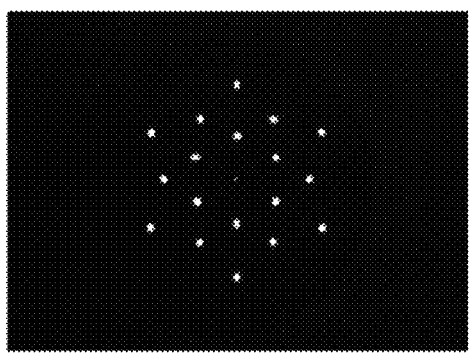
FIG. 3: depicts two frontal images with light spot patterns reflected by the cornea in the case of different fixations.
Figure 3:
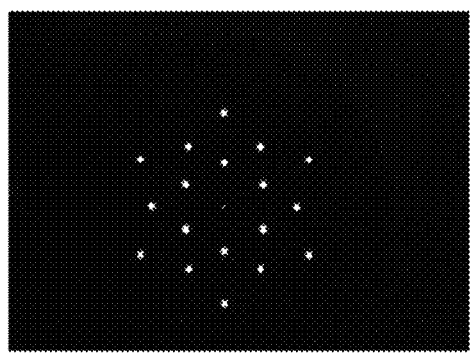

To this end, FIG. 3 shows two frontal images with light spot patterns that have been reflected by the cornea. Here, the light spot pattern is projected onto the eye along the optical axis of the measuring device. Accordingly, what can be gathered from the two image representations is that a correct fixation is only present in the left image representation. The light spot pattern in the right image representation is clearly shifted downward.

To record such frontal images, use can likewise be made of, for example, an IOLMaster 700 by Carl Zeiss Meditec AG. However, these frontal images are the result of the keratometer application included in the IOLMaster 700.

According to an example embodiment of the invention, a difference vector is calculated in method step f) for each frontal image recorded in method step c), said difference vector describing the deviations from the frontal image recorded in method step b).

To calculate the difference vectors, use is made of the circular ring fitted to the limbus or the pupil, with use for example being made of the distance between the center of the circular ring and the additionally generated reflection.

What should be taken into account when calculating the difference vectors is that the difference vectors to be calculated are dependent on the anterior chamber depth of the relevant eye.

The longer the anterior chamber depth, the greater the influence of the fixation on the offset vector, too. Here, the relationship can be modeled in simple multiplicative fashion, i.e., doubling the anterior chamber depth leads to a doubled threshold.

The geometric relationships only apply approximately to a real eye. However, the multiplicative influence of the anterior chamber depth on the length of the offset vector represents at least a good approximation and allows a simple adaptation of the threshold to the respective patient eye on the basis of its anterior chamber depth.

Using the proposed solution according to the invention, checking the fixation state is possible throughout by virtue of:
there being a check for correct fixation on the basis of the central retinal OCT scan, wherein this can be implemented manually or automatically and passively or actively with the cooperation of the patient.

The relative fixation information from suitable frontal images recorded at different times is compared to the relative fixation information from the time when the central retinal OCT scan was recorded, the latter supplying absolute fixation information. By way of example, this can be implemented by application of a suitable threshold for the length of the calculated difference vectors at the two recording times.

The fixation check of the central retinal OCT scan is only transferable to the recording times at which this threshold has not been exceeded. If the fixation is correct according to the central retinal OCT scan, it is also correct at these recording times.

In the very short time between two frontal images with relative fixation information, an identical fixation can be assumed if the length of the difference vector does not exceed a suitable threshold. Should the fixation be correct for the recording times of the two frontal images according to the transferred fixation check, the assumption can also be made that the fixation is correct in the intermediate time.

In general, a suitable threshold for this fixation check depends on the measurement task, in particular on the tolerance thereof for fixation deviations. It can be derived from a theoretical eye model or determined experimentally.

Figure 4:
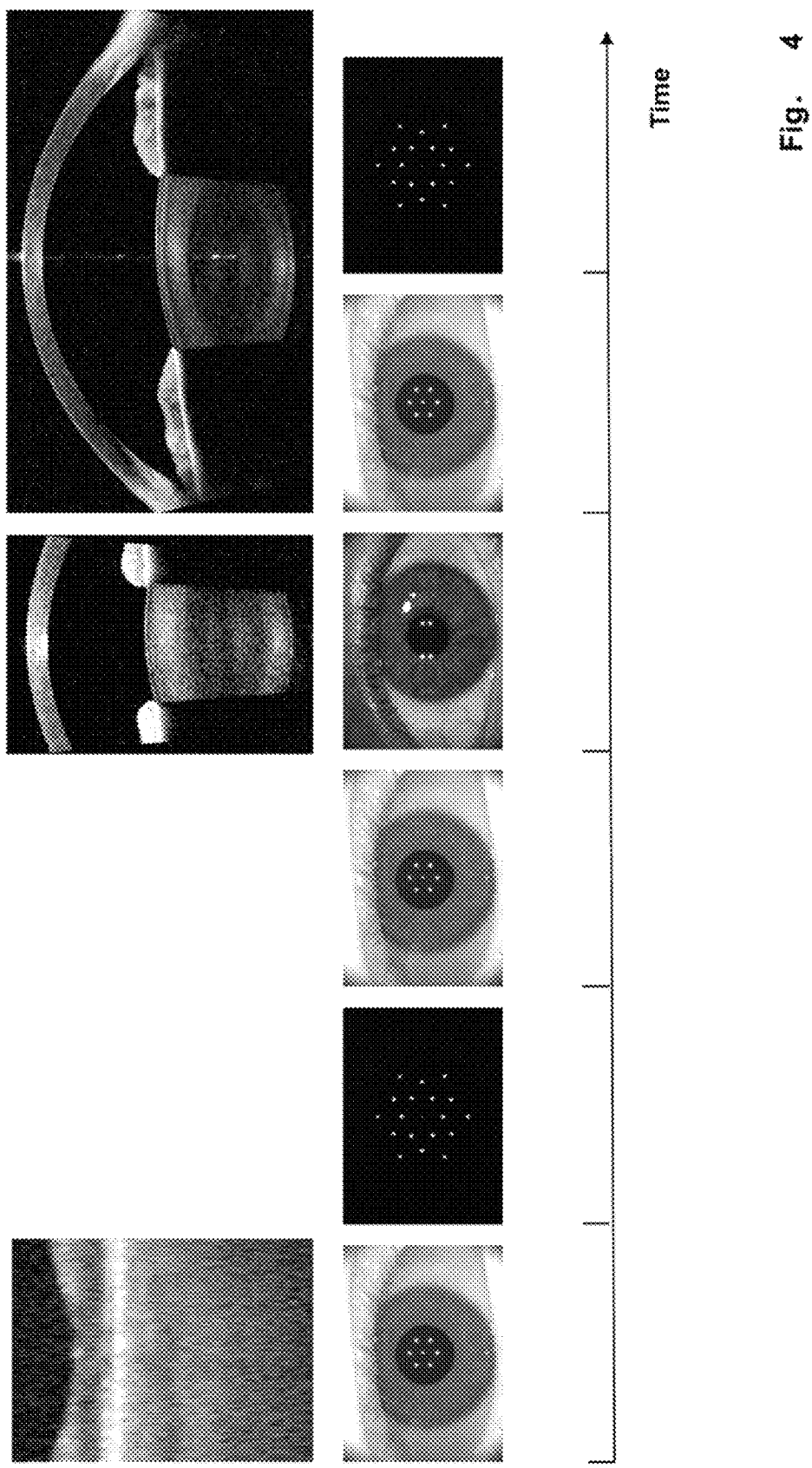
FIG. 4: depicts a possible recording sequence with a central retinal OCT scan and different frontal images for checking the fixation state throughout.

To this end, FIG. 4 shows a possible recording sequence with a central retinal OCT scan and different frontal images for checking the fixation state throughout.

A first frontal image under at least partly diffuse lighting (image representation bottom left) was recorded at the same time as the central retinal OCT scan (image representation top left). Then, further frontal images were recorded throughout in different lighting situations (image representations in the lower row).

While image representations 1, 3 and 5 in the lower row show frontal images in the case of at least partly diffuse lighting and an additional reflection on the cornea, image representations 2 and 6 are recordings of the keratometry application on its own. Image representation 4 shows a frontal image in a different lighting situation, with at least partly, diffuse lighting but without an additional reflection on the cornea.

The upper row depicts OCT recordings of different scanning modes.

The timeline shown is intended to document that the depicted image representations were recorded simultaneously (one below the other) and one after the other (side by side).

According to the invention, the calculated difference vectors can be used in the proposed method for the purposes of compensating the eye movement, for the purposes of which use is made of further measurement values, such as the anterior chamber depth, corneal radius and axis length.

Further, the fixation error can be determined from a sufficiently wide, 3-dimensional retinal OCT scan. To this end, too, use is made of further measurement values such as the anterior chamber depth, corneal radius and axis length.

Here, the fixation error at the time of this data recording is ascertained from the lateral displacement of the foveal pit and the axis length. This allows the fixation error to be compensated at this time, just as described in the previous paragraph.

Using the solution according to the invention, a method for capturing biometric measurement data of a patient's eye is made available, in which the fixation is monitored throughout the entire biometric measurement.

Here, monitoring the fixation is part of the recording of measurement data, for checking the quality of the recorded measurement data and, ideally, for compensating fixation errors, too.

The fixation is checked and/or compensated throughout, to be precise without this substantially extending the recording of the measurement data.

The decisive advantage of the proposed solution lies in the temporal transfer of the absolute fixation information by way of temporal meshing of different modalities for recording data.

This is implemented by complementing the absolute fixation information from a central retinal OCT scan with relative fixation information from other modalities, which are carried out continuously in parallel or in temporally closely alternating fashion with other modes of recording data.

There are probably a number of possibilities for the type of data recording with relative fixation information. What is decisive here is that there are structures at different distances from the measuring device, which move laterally relative to one another in the camera image in the case of a rotation of the eye.

In particular, the ascertained rotation can be refined, for example by rigid registration of free form surfaces from topography measurements of the corneal front side. This particularly holds true for patients with a sufficiently complicated cornea, which is often the case in the form of astigmatism, for example.

Using the proposed method, the fixation is monitored throughout the entire biometric measurement, as a result of which only the biometric measurement data captured at the correct fixation are used for the patient's eye.

In the case of multiple measurements, mean values could additionally be formed from the available biometric measurement values, as a result of which there can be an additional improvement in the quality of the recorded measurement data.

The invention claimed is:

1. A method for monitoring fixation of a patient's eye throughout capture of the patient's eye's biometric measurement data, in which information relating to the fixation is extracted, depending on different recording modes, from already available or additionally captured recordings and/or data, comprising:
   a) recording a central retinal OCT scan with absolute fixation information,
   b) recording a frontal image with relative fixation information at the same time as, or immediately before or after, the central retinal OCT scan with at least partly diffuse lighting,
   c) recording further frontal images with relative fixation information as continuously as possible over time,
   d) checking a fixation state on a basis of the central retinal OCT scan,
   e) should a correct fixation be present, Assuming the correct fixation for the frontal image recorded in method step b),
   f) calculating a difference vector for each frontal image recorded in method step c), said difference vector describing the deviations from the frontal image recorded in method step b),
   g) comparing the calculated difference vectors of the frontal images recorded in method step c) with a defined threshold, wherein
   h) a correct fixation for the recorded frontal images is assumed if the thresholds are undershot and no correct fixation is assumed if the thresholds are overshot and
   i) use is only made of the biometric measurement data captured just before, at the same time as or just after the frontal images with the correct fixation.

2. The method as claimed in claim 1, further comprising, generating an additional reflection on the cornea for the frontal image to be recorded in method step b).

3. The method as claimed in claim 2, wherein the additional reflection is produced proximate a vertex.

4. The method as claimed in claim 2, wherein the additional reflection is produced at a vertex.

5. The method as claimed in claim 2, wherein the generating the additional reflection on the cornea is implemented by application of a collimated light beam along an optical axis of a device.

6. The method as claimed in claim 1, wherein the frontal images are recorded as per method step c) depending on the recording modes at different lighting situations.

7. The method as claimed in claim 1, wherein a correct fixation is present in the result of method step d) if the central retinal OCT scan contains the foveal pit.

8. The method as claimed in claim 7, wherein an operator receives a notification if the central retinal OCT scan does not contain the foveal pit and there is no correct fixation in the result of method step d).

9. The method as claimed in claim 8, further comprising restarting the method with method step a), either by the operator or automatically.

10. The method as claimed in claim 7, further comprising determining fixation error from a sufficiently wide, 3-dimensional retinal OCT scan.

11. The method as claimed in claim 10, further comprising compensating for eye movement on a basis of the fixation error and further measurement values, selected from a group consisting of the anterior chamber depth, corneal radius and axis length.

12. The method as claimed in claim 1, further comprising fitting a circular ring to the limbus or the pupil for the calculation of the difference vectors as per method step f).

13. The method as claimed in claim 12, further comprising using a distance between a center of the circular ring and the additionally generated reflection for calculating the difference vectors as per method step f).

14. The method as claimed in claim 13, wherein the difference vectors to be calculated are dependent on anterior chamber depth of the patient's eye.

15. The method as claimed in claim 14, further comprising assuming a correct fixation for a time between two frontal images recorded immediately in succession, for which frontal images the calculated difference vectors as per method step h) undershoot a threshold.

16. The method as claimed in claim 1, further comprising assuming a correct fixation for a time between two frontal images recorded immediately in succession, for which frontal images the calculated difference vectors as per method step h) undershoot a threshold.

17. The method as claimed in claim 16, wherein the threshold to be used is derived from an eye model or determined experimentally.

18. The method as claimed in claim 1, further comprising using the calculated difference vectors to compensate for eye movement.

19. The method as claimed in claim 18, further comprising using further measurement values, chosen from a group consisting of anterior chamber depth, corneal radius and axis length, for compensating the eye movement.

20. The method as claimed in claim 1, further comprising determining fixation error from a sufficiently wide, 3-dimensional retinal OCT scan.

21. The method as claimed in claim 20, further comprising compensating for eye movement on a basis of the fixation error and further measurement values, selected from a group consisting of the anterior chamber depth, corneal radius and axis length.

* * * * *

UNITED STATES PATENT AND TRADEMARK OFFICE
CERTIFICATE OF CORRECTION

PATENT NO. : 11,766,171 B2
APPLICATION NO. : 16/962508
DATED : September 26, 2023
INVENTOR(S) : Ferid Bajramovic et al.

Page 1 of 1

It is certified that error appears in the above-identified patent and that said Letters Patent is hereby corrected as shown below:

In the Specification

Column 1, Line 10, delete "PCT/EP2019/051900" and insert --PCT/EP2019/051090--

Column 2, Line 53, delete "overshot and" and insert --overshot, and--

Column 3, Line 44, delete "overshot and" and insert --overshot, and--

In the Claims

Column 7, Line 58, delete "Assuming" and insert --assuming--

Column 8, Line 3, delete "overshot and" and insert --overshot, and--

Signed and Sealed this
Twenty-eighth Day of November, 2023

Katherine Kelly Vidal
*Director of the United States Patent and Trademark Office*